US010280236B2

(12) United States Patent
Kim et al.

(10) Patent No.: US 10,280,236 B2
(45) Date of Patent: May 7, 2019

(54) LIGAND COMPOUND, TRANSITION METAL COMPOUND AND CATALYST COMPOSITION INCLUDING THE TRANSITION METAL COMPOUND

(71) Applicant: LG CHEM, LTD., Seoul (KR)

(72) Inventors: A Rim Kim, Daejeon (KR); Dong Eun Kim, Daejeon (KR); Jin Sam Gong, Daejeon (KR); Seung Hwan Jung, Daejeon (KR); Hae Woong Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/121,157

(22) Filed: Sep. 4, 2018

(65) Prior Publication Data
US 2018/0371116 A1    Dec. 27, 2018

Related U.S. Application Data

(63) Continuation of application No. 15/323,595, filed as application No. PCT/KR2015/007760 on Jul. 24, 2015, now Pat. No. 10,093,755.

(30) Foreign Application Priority Data

Nov. 13, 2014 (KR) .................. 10-2014-0158273
Jul. 3, 2015 (KR) .................. 10-2015-0095336

(51) Int. Cl.
| | |
|---|---|
| *C07F 7/10* | (2006.01) |
| *C07F 17/00* | (2006.01) |
| *C08F 4/6592* | (2006.01) |
| *C08F 210/16* | (2006.01) |
| *C08F 4/76* | (2006.01) |
| *C07F 7/08* | (2006.01) |
| *C07F 7/28* | (2006.01) |
| *C08F 4/659* | (2006.01) |

(52) U.S. Cl.
CPC .................. *C08F 4/76* (2013.01); *C07F 7/08* (2013.01); *C07F 7/10* (2013.01); *C07F 7/28* (2013.01); *C07F 17/00* (2013.01); *C08F 4/6592* (2013.01); *C08F 210/16* (2013.01); *C08F 4/65908* (2013.01); *C08F 2420/02* (2013.01); *C08F 2420/06* (2013.01)

(58) Field of Classification Search
CPC .......... C07F 7/10; C07F 17/00; C08F 4/6592; C08F 210/16
See application file for complete search history.

(56) References Cited

U.S. PATENT DOCUMENTS

| | | |
|---|---|---|
| 5,064,802 A | 11/1991 | Stevens et al. |
| 6,015,916 A | 1/2000 | Sullivan et al. |
| 6,548,686 B2 | 4/2003 | Nabika et al. |
| 2002/0147286 A1 | 10/2002 | Resconi et al. |
| 2004/0023791 A1 | 2/2004 | Wang et al. |
| 2004/0259722 A1 | 12/2004 | Wang |
| 2007/0135623 A1 | 6/2007 | Voskoboynikov et al. |
| 2007/0225158 A1 | 9/2007 | Lee et al. |
| 2010/0087609 A1 | 4/2010 | Park et al. |
| 2011/0152529 A1 | 6/2011 | Lee et al. |
| 2011/0160413 A1 | 6/2011 | Lee et al. |
| 2011/0288249 A1 | 11/2011 | Voskoboynikov et al. |
| 2012/0202956 A1 | 8/2012 | Voskoboynikov et al. |
| 2013/0085246 A1 | 4/2013 | Kum et al. |
| 2013/0203949 A1 | 8/2013 | Lee et al. |
| 2013/0211020 A1 | 8/2013 | Lee et al. |
| 2013/0211021 A1 | 8/2013 | Lee et al. |
| 2013/0211023 A1 | 8/2013 | Lee |
| 2013/0211024 A1 | 8/2013 | Lee et al. |
| 2015/0011770 A1 | 1/2015 | Lee et al. |
| 2015/0045526 A1 | 2/2015 | Kum et al. |
| 2015/0094435 A1 | 4/2015 | Cho et al. |
| 2015/0361196 A1 | 12/2015 | Do et al. |

FOREIGN PATENT DOCUMENTS

| | | |
|---|---|---|
| CN | 103122042 A | 5/2013 |
| EP | 2 374 822 A2 | 10/2011 |
| JP | 2003-520869 A | 7/2003 |
| JP | 2006-502252 A | 1/2006 |
| JP | 2007-518834 A | 7/2007 |
| JP | 2013-533351 A | 8/2013 |
| KR | 10-2007-0098277 A | 10/2007 |

(Continued)

OTHER PUBLICATIONS

Chen et al., "A Novel Phenolate "Constrained Geometry" Catalyst System. Efficient Synthesis, Structural Characterization and α-Olefin Polymerization Catalysis", Organometallics 1996, 16, pp. 5958-5963.
Christie et al., "Novel Routes to Bidentate Cyclopentadienyl-Alkoxide Compleexes of Titanium: Synthesis of (η5-σ-C5R14CHR2CH2CR3R4O)TiCl2", Organometallics 1999, 18, pp. 348-359.
Extended European Search Report, dated Jul. 5, 2017, for European Application No. 15858880.6.
Gibson et al., "Advances in Non-Metallocene Olefin Polymerization Catalysis", Chem. Rev. 2003 103, pp. 283-315.

(Continued)

*Primary Examiner* — Caixia Lu
(74) *Attorney, Agent, or Firm* — Birch, Stewart, Kolasch & Birch, LLP

(57) ABSTRACT

The present invention relates to a novel ligand compound, a transition metal compound and a catalyst composition including the transition metal compound. The novel ligand compound and the transition metal compound of the present invention may be usefully used as the catalyst of a polymerization reaction for preparing an olefin polymer having a low density relative to a CGC catalyst. In addition, a product having a low melt index (MI) and a high molecular weight may be manufactured using the olefin polymer polymerized using the catalyst composition including the transition metal compound.

4 Claims, No Drawings

(56) References Cited

FOREIGN PATENT DOCUMENTS

| KR | 10-2008-0000355 A | 1/2008 |
|---|---|---|
| KR | 10-0820542 B1 | 4/2008 |
| KR | 10-2010-0067627 A | 6/2010 |
| KR | 10-0986301 B1 | 10/2010 |
| KR | 10-2015-0034652 A | 4/2015 |

OTHER PUBLICATIONS

Gielens et al., "Titanium Hydrocarbyl Complexes with a Linked Cyclopentadientyl-Alkoxide Ancillary Ligand; Participation of the Ligand in an Unusual Activation of a (Trimethylsilyl)methyl Group", Organometallics 1998, 17, pp. 1652-1654.

International Search Report issued in PCT/KR2015/007760 (PCT/ISA/210), dated Oct. 20, 2015.

Kim et al., "Preparation of Thiophene-Fused and Tetrahydroquinoline-Linked Cyclopentadienyl Titanium Complexes for Ethylene/α-Olefin Copolymerization", Catalysts 2013, vol. 3, pp. 104-124.

Rau et al., "Synthesis and application in high-pressure polymerization of a titanium complex with a linked cyclopentadienyl-phenoxide ligand", Journal of Organometallic Chemistry 608, 2000, pp. 71-75.

Ryabov et al., "Zirconium Complexes with Cyclopentadienyl Ligands Involving Fused a Thiophene Fragments", Organometallics 2002, 21, pp. 2842-2855.

Ryabov et al., "Constrained Geometry Complexes of Titanium (IV) and Zirconium (IV) Involving Cyclopentadienyl Fused to Thiophene Ring," Journal of Organometallic Chemistry, vol. 690, No. 19, 2005 (Oct. 1, 2005), Available online Aug. 5, 2005, pp. 4213-4221, XP027708856.

Turner et al., "Facile resolution of constrained geometry indenyl-phenoxide ligation", Chem. Comun., 2003, pp. 1034-1035.

Zhang et al., "Constrained Geometry Tetramethylcyclopentadienyl-phenoxytitanium Dichlorides: Template Synthesis, Structures, and Catalytic Properties for Ethylene Polymerization", Organometallics 2004, 23, pp. 540-546.

LIGAND COMPOUND, TRANSITION METAL COMPOUND AND CATALYST COMPOSITION INCLUDING THE TRANSITION METAL COMPOUND

CROSS-REFERENCE TO RELATED APPLICATIONS

This application is a Continuation of co-pending U.S. application Ser. No. 15/323,595, filed on Jan. 3, 2017, which is a National Stage of PCT/KR2015/007760, filed on Jul. 24, 2015, which claims the benefit of priority based on Korean Patent Application Nos. 10-2014-0158273, filed on Nov. 13, 2014, and 10-2015-0095336, filed on Jul. 3, 2015, and the entire contents disclosed in the Korean patent applications are hereby incorporated as a part of the specification.

TECHNICAL FIELD

The present invention relates to a ligand compound having a novel structure, a transition metal compound, and a catalyst composition including the transition metal compound.

BACKGROUND ART

[Me$_2$Si(Me$_4$C$_5$)NtBu]TiCl$_2$ (Constrained-Geometry Catalyst, hereinafter, will be abbreviated as CGC) was reported by Dow Co. in the early 1990s (U.S. Pat. No. 5,064,802), and excellent aspects of the CGC in the copolymerization reaction of ethylene and alpha-olefin may be summarized in the following two points when compared to commonly known metallocene catalysts: (1) at a high polymerization temperature, high activity is shown and a polymer having high molecular weight is produced, and (2) the copolymerization degree of alpha-olefin having large steric hindrance such as 1-hexene and 1-octene is excellent. In addition, as the various properties of the CGC during performing a polymerization reaction are gradually known, efforts on synthesizing the derivatives thereof and using the same as polymerization catalysts have been actively conducted in academy and industry.

As one approach, the synthesis and the polymerization of a metal compound introducing various bridges instead of a silicon bridge and a nitrogen substituent have been tried. Typical metal compounds known until now are illustrated as the following Compounds (1) to (4) (Chem. Rev. 2003, Vol. 103, pp 283).

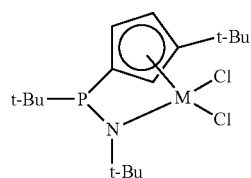

(1)

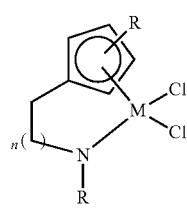

(2)

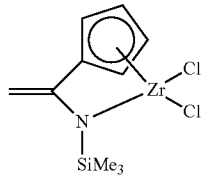

(3)

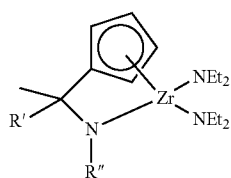

(4)

The above Compounds (1) to (4) introduce a phosphorous bridge (1), an ethylene or propylene bridge (2), a methylidene bridge (3) or a methylene bridge (4), respectively, instead of the silicon bridge of a CGC structure. However, with the above compounds, improved results on activity, copolymerization performance, etc. could not be obtained by applying to ethylene polymerization or copolymerization with alpha-olefin when compared to those obtained by applying the CGC.

In addition, as another approach, a compound composed of an oxido ligand instead of the amido ligand of the CGC has been synthesized, and some attempts on the polymerization using thereof have been conducted. Examples thereof are summarized as follows.

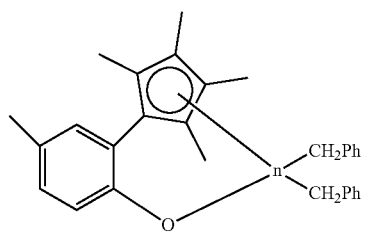

(5)

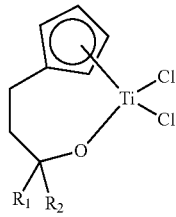

(6)

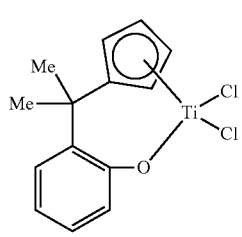

(7)

-continued (8)

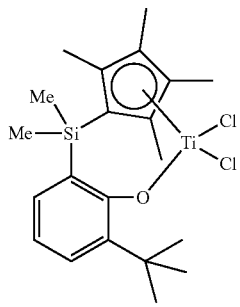

Compound (5) has been reported by T. J. Marks et al. and is characterized in that a cyclopentadiene (Cp) derivative and an oxido ligand are bridged via an ortho-phenylene group (*Organometallics* 1997, Vol. 16, pp 5958). A compound having the same bridged group and a polymerization using thereof have been reported by Mu et al. (*Organometallics* 2004, Vol. 23, pp 540). In addition, the bridging of an indenyl ligand and an oxido ligand by the same ortho-phenylene group has been reported by Rothwell et al. (*Chem. Commun.* 2003, pp 1034). Compound (6) has been reported by Whitby et al. and is characterized in that a cyclopentadienyl ligand and an oxido ligand are bridged by three carbon atoms (*Organometallics* 1999, 18, 348). The above catalysts have been reported to show activity in a syndiotactic polystyrene polymerization. Similar compounds have been also reported by Hessen et al. (*Organometallics* 1998, Vol. 17, pp 1652). Compound (7) has been reported by Rau et al. and is characterized in showing activity in ethylene polymerization and ethylene/1-hexene copolymerization at a high temperature and a high pressure (210° C., 150 MPa) (*J. Organomet. Chem.* 2000, Vol. 608, pp 71). In addition, the synthesis of a catalyst (8) having a similar structure as that of Compound (7) and a polymerization using the same at a high temperature and a high pressure have been filed by Sumitomo Co. (U.S. Pat. No. 6,548,686). However, not many catalysts among the above attempts are practically applied in commercial plants.

Accordingly, a catalyst showing further improved polymerization performance is required, and a simple preparation method of the catalyst is required.

DISCLOSURE OF THE INVENTION

Technical Problem

According to an aspect of the present invention, a novel transition metal compound is provided.

According to another aspect of the present invention, a novel ligand compound is provided.

According to further another aspect of the present invention, a catalyst composition including the transition metal compound is provided.

Technical Solution

According to an aspect of the present invention, there is provided a transition metal compound represented by the following Formula 1.

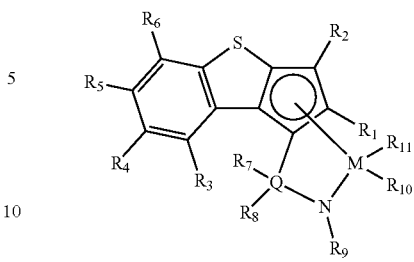

[Formula 1]

In the above Formula 1, $R_1$ to $R_6$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, $R_7$ and $R_8$ are each independently hydrogen; alkyl having 1 to 20 carbon atoms; alkenyl having 2 to 20 carbon atoms; aryl having 6 to 20 carbon atoms; alkylaryl having 6 to 20 carbon atoms; arylalkyl having 7 to 20 carbon atoms; alkyl amido having 1 to 20 carbon atoms; aryl amido having 6 to 20 carbon atoms; or alkylidene having 1 to 20 carbon atoms, $R_9$ is hydrogen; alkyl having 1 to 20 carbon atoms; alkenyl having 2 to 20 carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms, at least two adjacent elements of $R_1$ to $R_9$ may be connected to each other to form a ring, $R_{10}$ and $R_{11}$ are each independently hydrogen, halogen, alkyl having 1 to 20 carbon atoms, alkenyl having 2 to 20 carbon atoms, aryl having 6 to 20 carbon atoms, alkylaryl having 7 to 20 carbon atoms; arylalkyl having 7 to 20 carbon atoms, alkylamino having 1 to 20 carbon atoms, arylamino having 6 to 20 carbon atoms, or alkylidene having 1 to 20 carbon atoms, Q is Si, C, N, P, or S, and M is a transition metal in group 4.

According to another aspect of the present invention, there is provided a ligand compound represented by the following Formula 2.

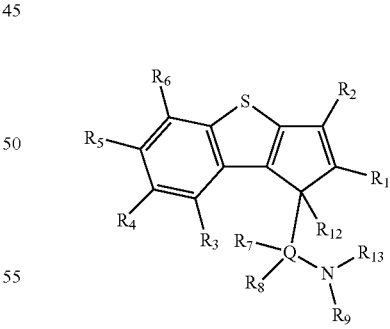

[Formula 2]

In Formula 2, $R_1$ to $R_6$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, $R_7$ and $R_8$ are each independently hydrogen; alkyl having 1 to 20 carbon atoms; alkenyl having 2 to 20 carbon atoms; aryl having 6 to 20 carbon atoms; alkylaryl having 6 to 20 carbon atoms; arylalkyl having 7 to 20 carbon atoms; alkyl amido having 1 to 20 carbon atoms; aryl amido having 6 to 20 carbon atoms; or alkylidene having 1 to 20 carbon atoms, $R_9$ is hydrogen; alkyl having 1 to 20 carbon atoms; alkenyl having 2 to 20 carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms, at least two adjacent elements of $R_1$ to $R_9$ may be connected to each other to form a ring, $R_{12}$ and $R_{13}$ are each independently hydrogen, Q is Si, C, N, P, or S.

According to further another aspect of the present invention, there is provided a catalyst composition including the transition metal compound of the above Formula 1.

Advantageous Effects

The novel ligand compound and the transition metal compound according to the present invention may be usefully used as a catalyst in a polymerization reaction for preparing an olefin polymer having a high molecular weight in a low density region relative to a [Me$_2$Si(Me$_4$C$_5$)NtBu]TiCl$_2$ (Constrained-Geometry Catalyst, hereinafter will be abbreviated as CGC) catalyst.

BEST MODE FOR CARRYING OUT THE INVENTION

Hereinafter, the present invention will be described in more detail to assist the understanding of the present invention.

It will be understood that words or terms used in the specification and claims shall not be interpreted as the meaning used in common or defined dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

According to an aspect of the present invention, a transition metal compound represented by the following Formula 1 is provided.

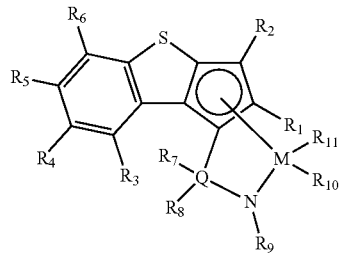

[Formula 1]

In the above Formula 1, $R_1$ to $R_6$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, $R_7$ and $R_8$ are each independently hydrogen; alkyl having 1 to 20 carbon atoms; alkenyl having 2 to 20 carbon atoms; aryl having 6 to 20 carbon atoms; alkylaryl having 6 to 20 carbon atoms; arylalkyl having 7 to 20 carbon atoms; alkyl amido having 1 to 20 carbon atoms; aryl amido having 6 to 20 carbon atoms; or alkylidene having 1 to 20 carbon atoms, $R_9$ is hydrogen; alkyl having 1 to 20 carbon atoms; alkenyl having 2 to 20 carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms, at least two adjacent elements of $R_1$ to $R_9$ may be connected to each other to form a ring, $R_{10}$ and $R_{11}$ are each independently hydrogen, halogen, alkyl having 1 to 20 carbon atoms, alkenyl having 2 to 20 carbon atoms, aryl having 6 to 20 carbon atoms, alkylaryl having 7 to 20 carbon atoms; arylalkyl having 7 to 20 carbon atoms, alkylamino having 1 to 20 carbon atoms, arylamino having 6 to 20 carbon atoms, or alkylidene having 1 to 20 carbon atoms, Q is Si, C, N, P, or S, and M is a transition metal in group 4.

The transition metal compound of Formula 1 described in the present disclosure forms a structure in which benzothiophene fused cyclopentadiene by the bonding of a ring shape and an amido group (N—R$_9$) make stable bridge bond via Q (Si, C, N, or P) and a transition metal in group 4 makes a coordination bond.

By applying the catalyst composition to an olefin polymerization, polyolefin having high activity, high molecular weight and high copolymerization degree at a high polymerization temperature may be produced. In particular, due to the structural properties of the catalyst, a large amount of alpha-olefin as well as polyethylene having a linear and low density of 0.850 g/cc to 0.930 g/cc level may be introduced, and a polymer (elastomer) in a very-low-density region less than 0.910 g/cc may be produced.

In the present disclosure, alkyl and alkenyl are alkyl having 1 to 20 carbon atoms and alkenyl having 2 to 20 carbon atoms, respectively, and may be linear or branched.

In the present disclosure, aryl includes a monocyclic or polycyclic aryl, and particularly includes phenyl, naphthyl, anthryl, phenanthryl, chrysenyl, pyrenyl, etc.

$R_9$ may be substituted or unsubstituted, and in the case of the substituted $R_9$, a substituent may be, for example, alkyl having 1 to 20 carbon atoms, hydrocarbyl having 1 to 20 carbon atoms, alkoxy having 1 to 20 carbon atoms, or aryloxy having 6 to 20 carbon atoms.

In particular, according to an embodiment of the present invention, in Formula 1, $R_1$ to $R_6$ are each independently hydrogen; alkyl having 1 to 20 carbon atoms; aryl having 6 to 20 carbon atoms; alkylaryl having 7 to 20 carbon atoms; or arylalkyl having 7 to 20 carbon atoms, $R_7$ and $R_8$ are each independently hydrogen; alkyl having 1 to 20 carbon atoms; aryl having 6 to 20 carbon atoms; or alkylaryl having 6 to 20 carbon atoms, $R_9$ is hydrogen; alkyl having 1 to 20 carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms, at least two adjacent elements of $R_1$ to $R_9$ may be connected to each other to form an aliphatic ring having 5 to 20 carbon atoms or an aromatic ring having 6 to 20 carbon atoms, the aliphatic ring or the aromatic ring being substituted with halogen, alkyl having 1 to 20 carbon atoms, alkenyl having 2 to 20 carbon atoms, or aryl having 6 to 20 carbon atoms, and Q may be Si, C, N, or P.

More particularly, according to an embodiment of the present invention, in Formula 1, $R_1$ to $R_6$ are each independently hydrogen; alkyl having 1 to 20 carbon atoms; or aryl having 6 to 20 carbon atoms, $R_7$ and $R_8$ are each independently hydrogen; alkyl having 1 to 20 carbon atoms; or aryl having 6 to 20 carbon atoms, $R_9$ is alkyl having 1 to 20 carbon atoms; aryl having 6 to 20 carbon atoms; arylalkoxy having 7 to 20 carbon atoms; or arylalkyl having 7 to 20 carbon atoms, and Q may be Si.

More particularly, according to an embodiment of the present invention, $R_1$ and $R_2$ may be the same or different and each independently alkyl having 1 to 6 carbon atoms.

According to an embodiment of the present invention, $R_1$ and $R_2$ may be methyl, ethyl or propyl.

According to an embodiment of the present invention, $R_3$ to $R_6$ may be the same or different and each independently hydrogen; alkyl having 1 to 20 carbon atoms; or aryl having 6 to 20 carbon atoms.

According to an embodiment of the present invention, $R_3$ to $R_6$ may be the same or different and each independently hydrogen, methyl or ethyl.

According to an embodiment of the present invention, $R_7$ and $R_8$ may be each independently hydrogen; alkyl having 1 to 20 carbon atoms; or aryl having 6 to 20 carbon atoms.

According to an embodiment of the present invention, $R_9$ may be methyl, ethyl, isopropyl, tertiary butyl, isobutyl, isopropyl, phenyl, methoxyphenyl, ethoxyphenyl, dimethylphenyl, or diethylphenyl.

According to an embodiment of the present invention, $R_{10}$ and $R_{11}$ may be the same or different and each independently hydrogen, halogen, alkyl having 1 to 20 carbon atoms, or alkenyl having 2 to 20 carbon atoms.

According to an embodiment of the present invention, M may be Ti, Hf, or Zr.

In addition, according to an embodiment, the compound represented by Formula 1 may be represented by one of the following formulae.

[Formula 1-1]

[Formula 1-2]

[Formula 1-3]

In order to achieve the second aspect of the present invention, a ligand compound represented by the following Formula 2 may be provided.

[Formula 2]

In Formula 2, $R_1$ to $R_6$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, $R_7$ and $R_8$ are each independently hydrogen; alkyl having 1 to 20 carbon atoms; alkenyl having 2 to 20 carbon atoms; aryl having 6 to 20 carbon atoms; alkylaryl having 6 to 20 carbon atoms; arylalkyl having 7 to 20 carbon atoms; alkyl amido having 1 to 20 carbon atoms; aryl amido having 6 to 20 carbon atoms; or alkylidene having 1 to 20 carbon atoms, $R_9$ is hydrogen; alkyl having 1 to 20 carbon atoms; alkenyl having 2 to 20 carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms, at least two adjacent elements of $R_1$ to $R_9$ may be connected to each other to form a ring, $R_{12}$ and $R_{13}$ are each independently hydrogen, and Q is Si, C, N, P, or S.

The ligand compound of Formula 2 described in the present disclosure has a stably bridged structure by benzothiophene fused cyclopentadiene via the bonding to a ring shape, and an amido group (N—$R_9$) via Q (Si, C, N, or P).

In the ligand compound, the definition of $R_1$ to $R_9$ of the compound represented by Formula 2 may be the same as the definition in the compound represented by Formula 1 which is the transition metal compound.

According to another embodiment of the present invention, the compound represented by Formula 1 is preferably represented by one of the following formulae.

[Formula 2-1]

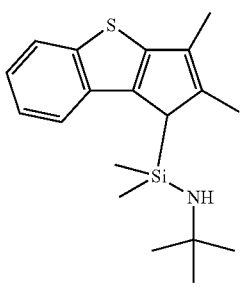

[Formula 2-2]

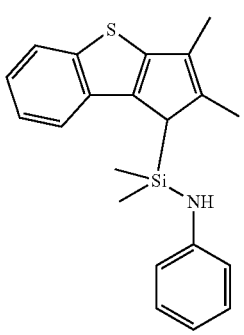

[Formula 2-3]

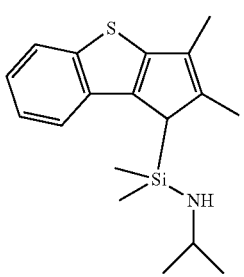

The transition metal compound of Formula 1 and the ligand compound of Formula 2 are preferably used for the preparation of a catalyst for the polymerization of an olefin monomer, however embodiments are not limited thereto, and the compounds may be applied to all fields utilizing the transition metal compound.

The ligand compound represented by Formula 2 of the present invention may be prepared by the following Reaction 1.

[Reaction 1]

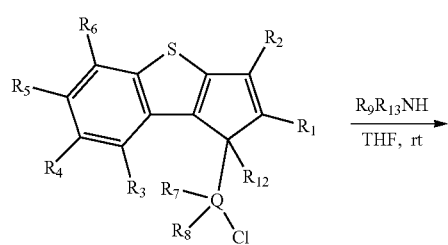

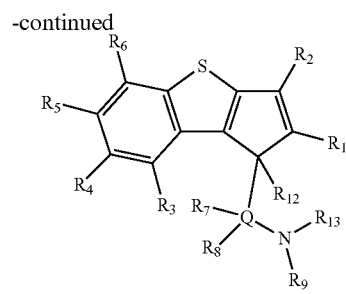

In Reaction 1, $R_1$ to $R_9$, $R_{12}$, $R_{13}$ and Q are the same as defined in Formula 2.

Particularly, the ligand compound of Formula 2 may be prepared by the following steps a) and b):

a) a step of preparing a compound represented by the following [Formula 3] by reacting a compound represented by the following [Formula 4] with a compound represented by the following [Formula 5]; and b) a step of preparing a compound represented by the following [Formula 2] by reacting a compound represented by the following [Formula 3] with a compound represented by the following [Formula 6].

[Formula 4]

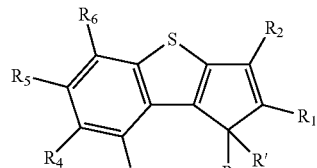

[Formula 5]

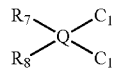

[Formula 3]

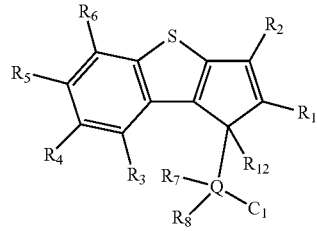

[Formula 6]

$R_9R_{13}NH$

[Formula 2]

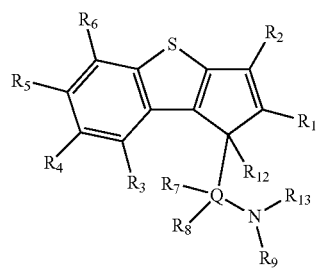

In the above formulae, $R_1$ to $R_9$, $R_{12}$, $R_{13}$ and Q are the same as defined in Formula 2, and R' is hydrogen.

The transition metal compound represented by Formula 1 of the present invention may be prepared using the ligand compound represented by Formula 2 according to the following Reaction 2.

[Reaction 2]

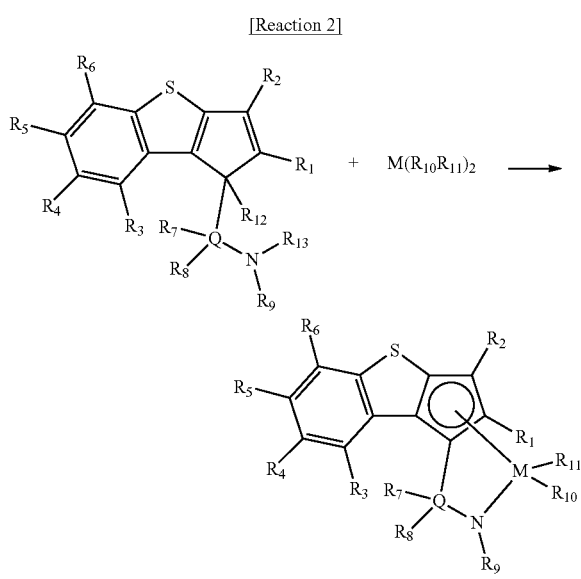

In the above reaction, $R_1$ to $R_{13}$, Q and M are the same as defined in Formula 1 or 2.

According to an embodiment of the present invention, the transition metal compound represented by Formula 1 may have a coordination bond of a transition metal in group 4 with the compound represented by Formula 2 as a ligand.

In particular, as in Reaction 2, the transition metal compound of Formula 1 in which the transition metal in group 4 makes a coordination bond with the compound represented by Formula 2 as a ligand may be obtained via the reaction of a compound represented by Formula 2 with a compound represented by the following Formula 7 as a metal precursor and an organolithium compound, and recrystallization.

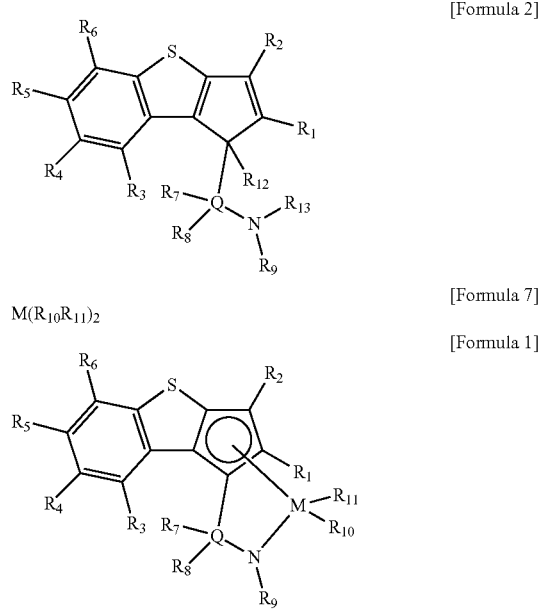

[Formula 2]

$M(R_{10}R_{11})_2$ [Formula 7]

[Formula 1]

In the above formulae, $R_1$ to $R_{13}$, Q and M are the same as defined in Formula 1.

In Reaction 2, the organolithium compound may be, for example, selected from the group consisting of n-butyllithium, sec-butyllithium, methyllithium, ethyllithium, isopropyllithium, cyclohexyllithium, allyllithium, vinyllithium, phenyllithium and benzyllithium.

The compound represented by Formula 2 and the compound represented by Formula 5 may be mixed in a molar ratio of 1:0.8 to 1:1.5, and preferably, 1:1.0 to 1:1.1.

In addition, the organolithium compound may be used in an amount ratio of 180 to 250 parts by weight on the basis of 100 parts by weight of the compound represented by Formula 2.

In the preparation method according to an embodiment of the present invention, the reaction may preferably be performed at a temperature range of −80° C. to 140° C. for 1 to 48 hours.

According to an embodiment of the present invention, the compound represented by Formula 3 and the compound represented by Formula 6 may be mixed in a molar ratio of 1:0.8 to 1:5.0, preferably, 1:0.9 to 1:4.5, and more preferably, 1:1 to 1:4.0.

In addition, according to an embodiment of the present invention, the compound represented by Formula 4 and the compound represented by Formula 5 may be mixed in a molar ratio of 1:0.8 to 1:5.0, preferably, 1:0.9 to 1:4.0, and more preferably, 1:1 to 1:3.0.

In addition, the reaction may preferably be performed at a temperature range of −80° C. to 140° C. for 1 to 48 hours.

The present invention also provides a catalyst composition including the compound of Formula 1.

The catalyst composition may further include a co-catalyst. The co-catalyst may be any one known in this technical field.

For example, the catalyst composition may further include at least one of the following Formulae 8 to 10 as the co-catalyst.

$$—[Al(R_{22})—O]_a—$$ [Formula 8]

in the above formula, each $R_{22}$ is independently a halogen radical; a hydrocarbyl radical having 1 to 20 carbon atoms; or hydrocarbyl radical having 1 to 20 carbon atoms, and substituted with halogen; and a is an integer of 2 or more;

$$D(R_{22})_3$$ [Formula 9]

in the above formula, D is aluminum or boron; and each $R_{22}$ is independently the same as defined above;

$$[L-H]^+[Z(A)_4]^- \text{ or } [L]^+[Z(A)_4]^-$$ [Formula 10]

in the above formula, L is a neutral or a cationic Lewis acid; H is a hydrogen atom; Z is an element in group 13; each A is independently aryl having 6 to 20 carbon atoms or alkyl having 1 to 20 carbon atoms, where at least one hydrogen atom may be independently substituted with a substituent; and the substituent is halogen, hydrocarbyl having 1 to 20 carbon atoms, alkoxy having 1 to 20 carbon atoms or aryloxy having 6 to 20 carbon atoms.

As a preparation method of the catalyst composition, a first preparation method including a step of obtaining a mixture by contacting the transition metal compound represented by the above Formula 1 with a compound represented by the above Formula 8 or 9; and a step of adding a compound represented by the above Formula 10 to the mixture is provided.

Also, a second preparation method of the catalyst composition by contacting the transition metal compound represented by the above Formula 1 and the compound represented by the above Formula 10, is provided.

In the first method of the preparation methods of the catalyst composition, the molar ratio of the compound represented by the above Formula 8 or 9 with respect to the transition metal compound represented by the above Formula 1 is preferably from 1:2 to 1:5,000, more preferably, from 1:10 to 1:1,000, and most preferably, from 1:20 to 1:500.

Meanwhile, the molar ratio of the compound represented by Formula 10 with respect to the transition metal compound represented by Formula 1 is preferably from 1:1 to 1:25, more preferably, from 1:1 to 1:10, and most preferably, from 1:1 to 1:5.

In the case that the molar ratio of the compound represented by the above Formula 8 or 9 with respect to the transition metal compound of Formula 1 is less than 1:2, the amount of an alkylating agent is very small, and the alkylation of a metal compound may be incompletely attained, and in the case that the molar ratio exceeds 1:5,000, the metal compound may be alkylated, however a side reaction between the remaining alkylating agent and the activating agent of the above Formula 10 may be performed, and the activation of the alkylated metal compound may be incompletely attained. In addition, in the case that the molar ratio of the compound represented by Formula 10 with respect to the transition metal compound of Formula 2 is less than 1:1, the amount of the activating agent is relatively small, the activation of the metal compound may be incompletely performed, and the activity of the catalyst composition may be deteriorated. In the case that the molar ratio exceeds 1:25, the activation of the metal compound may be completely performed, however the excessive activating agent remained may increase the production cost of the catalyst composition, or the purity of the polymer thus prepared may be deteriorated.

In the second method of the preparation methods of the catalyst composition, the molar ratio of the compound represented by the above Formula 10 with respect to the transition metal compound of the above Formula 1 is preferably from 1:1 to 1:500, more preferably, from 1:1 to 1:50, and most preferably, from 1:2 to 1:25. In the case that the molar ratio is less than 1:1, the amount of the activating agent is relatively small, the activation of the metal compound may be incompletely performed, and the activity of the catalyst composition thus prepared may be deteriorated. In the case that the molar ratio exceeds 1:500, the activation of the metal compound may be completely performed, however the excessive activating agent remained may increase the unit cost of the catalyst composition, or the purity of the polymer thus prepared may be deteriorated.

As a reaction solvent used during the preparation of the composition, a hydrocarbon solvent such as pentane, hexane, heptane, etc, or an aromatic solvent such as benzene, toluene, etc. may be used, however exemplary embodiments of the present invention are not limited thereto, and all solvents used in this field may be used.

In addition, the transition metal compound of Formula 1 and the co-catalyst may be used as a supported type by a support. Silica or alumina may be used as the support.

The compound represented by the above Formula 8 is not specifically limited only if alkylaluminoxane is used. Preferably, the compound includes methylaluminoxane, ethylaluminoxane, isobutylaluminoxane, butylaluminoxane, etc., and the methylaluminoxane is a particularly preferable compound.

The compound represented by the above Formula 9 is not specifically limited and preferably includes trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, etc., and particularly preferable compound is selected from the trimethylaluminum, the triethylaluminum, and the triisobutylaluminum.

Examples of the compound represented by the above Formula 10 includes triethylammoniumtetraphenylboron, tributylammoniumtetraphenylboron, trimethylammoniumtetraphenylboron, tripropylammoniumtetraphenylboron, trimethylammoniumtetra(p-tolyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra(p-trifluoromethylphenyl)aluminum, tributylammoniumtetrapentafluorophenylaluminum, N,N-diethylaniliniumtetraphenylaluminum, N,N-diethylaniliniumtetraphenylaluminum, N,N-diethylaniliniumtetrapentafluorophenylaluminum, diethylammoniumtetrapentatetraphenylaluminum, triphenylphosphoniumtetraphenylaluminum, trimethylphosphoniumtetraphenylaluminum, triethylammoniumtetraphenylaluminum, tributylammoniumtetraphenylaluminum, trimethylammoniumtetraphenylboron, tripropylammoniumtetraphenylboron, trimethylammoniumtetra(p-tolyl)boron, tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, triphenylcarboniumtetra(p-trifluoromethylphenyl)boron, triphenylcarboniumtetrapentafluorophenylboron, etc.

A polyolefin homopolymer or copolymer may be prepared by contacting the catalyst composition including the transition metal compound of Formula 1; and at least one compound selected from the compounds represented by Formulae 8 to 10, with at least one olefin monomer.

The most preferable preparation process using the catalyst composition is a solution process. In the case that the composition is used together with an inorganic support such as silica, a slurry process or a gas phase process may be also applied.

In the preparation process, the activating catalyst composition may be injected after being dissolved or diluted in an aliphatic hydrocarbon solvent having 5 to 12 carbon atoms such as pentane, hexane, heptane, nonane, decane and an isomer thereof, an aromatic hydrocarbon solvent such as toluene and benzene, or a hydrocarbon solvent substituted with a chlorine atom such as dichloromethane and chlorobenzene. The solvent may preferably be used after removing a small amount of water or air, which functions as a catalyst poison, by treating with a small amount of alkylaluminum, and may be used by further using a co-catalyst.

The olefin monomer polymerizable using the metal compound and the co-catalyst may include ethylene, alpha-olefin, cyclic olefin, etc., and a diene olefin monomer, a triene olefin monomer, etc. having at least two double bonds may also be polymerized. Particular examples of the monomer may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-icocene, norbornene, norbornadiene, ethylidenenorbornene, phenylnorbornene, vinylnorbornene, dicyclopentadiene, 1,4-butadiene, 1,5-pentadiene, 1,6-hexadiene, styrene, alpha-methylstyrene, divinylbenzene, 3-chloromethylstyrene, etc. At least two of these monomers may be mixed and copolymerized.

Particularly, in the preparation method of the present invention using the catalyst composition, a copolymer having high molecular weight and a polymer density of 0.89 g/cc or less may be prepared in a copolymerization reaction of monomers such as ethylene and 1-octene having large steric hindrance at a high reaction temperature of 90° C. or more.

According to an embodiment of the present invention, the polymer prepared by the preparation method of the present invention has a density of less than 0.90 g/cc.

According to an embodiment of the present invention, the polymer prepared by the preparation method of the present invention has a density of 0.88 g/cc or less.

According to an embodiment of the present invention, the polymer prepared by the preparation method of the present invention has a density of less than 0.87 g/cc.

In addition, according to an embodiment of the present invention, in the case that the polymer is prepared using the transition metal catalyst of Formula 1, the peak of Tm (melting temperature) may have a single phase or two peaks.

Tm may be obtained using a differential scanning calorimeter 6000 (DSC) manufactured by PerkinElmer Co., and may be obtained by measuring the apex of a DSC curve as a melting point after elevating the temperature of the polymer to 100° C., maintaining the temperature for 1 minute, decreasing the temperature to −100° C., and then, elevating the temperature again.

According to an embodiment of the present invention, the polymer prepared by the preparation method of the present invention has Tm of 92 or less.

According to an embodiment of the present invention, the polymer prepared by the preparation method of the present invention, Tm may exhibit one or two peaks.

According to an embodiment of the present invention, the polymer prepared by the preparation method of the present invention may have melt index (MI) of 20 or less.

According to an embodiment of the present invention, the polymer prepared by the preparation method of the present invention may have melt index (MI) of 18 or less.

According to an embodiment of the present invention, the polymer prepared by the preparation method of the present invention may have melt index (MI) of 15 or less.

In the case that the melt index is 20 or less, a polymer having a high molecular weight may be prepared, and the polymer may be usefully used as a multilayer film for coating requiring a polymer having a high molecular weight. Here, the multilayer film for coating is not specifically limited, however may be a film for sunlight or a film for a laminated glass.

Hereinafter, the present invention will be explained more particularly referring to the following embodiments. The embodiments are illustrated for assisting the understanding of the present invention, and the scope of the present invention is not limited thereto.

Synthesis of Ligand and Transition Metal Compound

Organic reagents and solvents were purchased from Aldrich Co. and used after purification by a standard method unless otherwise mentioned. In all steps of syntheses, air and humidity were blocked to increase the reproducibility of experiments. In Formula 1, a compound substituted with tetramethyl cyclobutadiene among ketone compounds was synthesized according to a document [*Organometallics* 2002, Vol. 21, pp 2842-2855], and $Me_2Si(Me_4C_5)NtBu]TiMeI_2$ (Constrained-Geometry Catalyst, CGC, hereinafter will be abbreviated as CGC) was synthesized according to U.S. Pat. No. 6,015,916.

Synthesis of Ligand Compounds

Synthetic Example 1: Synthesis of N-tert-butyl-1-(2,3-dimethyl-1H-benzo[b]cyclopenta[d]thiophen-1l-yl)-1,1-dimethylsilanamine After weighing and adding 330 mg (0.12 mmol) of the compound of following Formula 3 ($R_1$, $R_2$, $R_7$ and $R_8$ are methyl, $R_3$ to $R_6$ and $R_{12}$ are hydrogen) to a 100 ml, Schlenk flask, 20 ml of hexane was injected. $tBuNH_2$ (4 eq, 0.47 ml) was added thereto at room temperature, followed by reacting at room temperature for three days. After finishing the reaction, the product thus obtained was filtered. Solvents were dried to obtain 345 mg (93% yield) of a target compound represented by the following Formula 2-1 as an orange liquid.

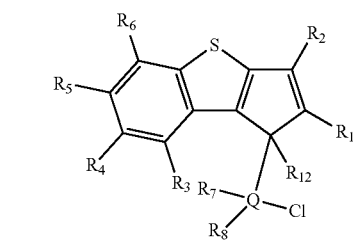

[Formula 3]

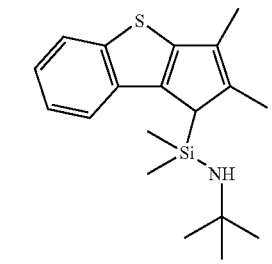

[Formula 2-1]

$^1$H NMR (in $C_6D_6$, 500 MHz): 7.82 (d, 1H), 7.69 (d, 1H), 7.27 (t, 1H), 7.03 (t, 1H), 3.39 (s, 1H), 2.03 (s, 3H), 1.99 (s, 3H), 1.04 (s, 9H), 0.07 (s, 3H), −0.11 (s, 3H).

Synthetic Example 2: Synthesis of N-phenyl-1-(2,3-dimethyl-1H-benzo[b]cyclopenta[d]thiophen-1-yl)-1,1-dimethylsilanamine After weighing and adding 710 mg (2.42 mmol) of the same compound of Formula 3 described in Synthetic Example 1 to a 100 ml, Schlenk flask, 10 ml of hexane was injected. Aniline (1.5 eq, 0.33 ml) was added at room temperature, followed by reacting for three days. After finishing the reaction, the product thus obtained was filtered. Solvents were dried to obtain 560 mg (66% yield) of a target compound represented by the following Formula 2-2 as an orange liquid.

[Formula 2-2]

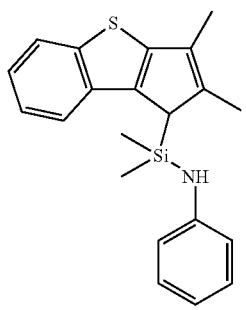

$^1$H NMR (in $C_6D_3$, 500 MHz): 7.55 (t, 2H), 7.19 (m, 3H), 7.01 (t, 1H), 6.82 (t, 1H), 6.65 (m, 2H), 3.69 (s, 1H), 1.93 (s, 3H), 1.88 (s, 3H), −0.05 (s, 3H), −0.16 (s, 3H).

Synthetic Example 3: Synthesis of N-isopropyl-1-(2,3-dimethyl-1H-benzo[b]cyclopenta[d]thiophen-1-yl)-1,1-dimethylsilanamine After weighing and adding 240 mg (0.82 mmol) of the same compound of Formula 3 described in Synthetic Example 1 to a 100 ml, Schlenk flask, 10 ml of THF was injected. The Schlenk flask was immersed into a bath of −30 for 30 minutes, while stirring. Then, isopropylamine (0.14 mg, 1.62 mmol) was dissolved in THF (8 ml) and was slowly added to the flask under an argon atmosphere. Then, the temperature was elevated to room temperature, followed by filtrating with hexane. Solvents in the filtrate were dried to obtain 240 mg (93% yield) of a target compound represented by the following Formula 2-3 as a yellow liquid.

[Formula 2-3]

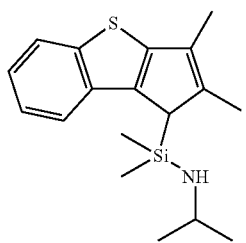

$^1$H NMR (in $C_6D_6$, 500 MHz): 7.82 (d, 1H), 7.71 (d, 1H), 7.28 (t, 1H), 7.04 (t, 1H), 3.38 (s, 1H), 1.99 (s, 6H), 0.91 (d, 3H), 0.85 (d, 3H), −0.03 (s, 3H), −0.09 (s, 3H).

Preparation of Transition Metal Compound

Preparation Example 1: Synthesis of Transition Metal Compound Represented by Formula 1-1

To a 20 ml, Schlenk flask, a ligand compound (260 mg, 0.80 mmol/1.0 eq) obtained in Synthetic Example 1 and represented by Formula 2-1 and 6.0 ml (0.1 M) of MTBE were added and stirred first. Then, n-BuLi (0.65 ml, 2.03 eq, 2.5 M in hexane) was added thereto at −40° C., followed by reacting at room temperature overnight. After that, MeMgBr (0.6 ml, 2.5 eq, 3.0 M in diethyl ether) was slowly added thereto dropwisely at −40° C., and $TiCl_4$ (0.8 ml, 1.0 eq, 1.0 M in toluene) was added, followed by reacting at room temperature overnight. After that, a reaction mixture was passed through Celite using hexane for filtering. Solvents were dried to obtain 170 mg (53% yield) of a transition metal compound represented by the following Formula 1-1 as a brown solid.

[Formula 1-1]

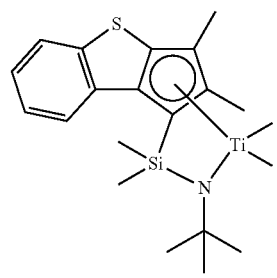

$^1$H NMR (in $CDCl_3$, 500 MHz): 7.99 (d, 1H), 7.47 (d, 1H), 7.10 (t, 1H), 6.97 (t, 1H), 2.12 (s, 3H), 1.89 (s, 3H), 1.46 (s, 9H), 0.67 (s, 3H), 0.59 (s, 3H), 0.51 (s, 3H), 0.10 (s, 3H).

Preparation Example 2: Synthesis of Transition Metal Compound Represented by Formula 1-2

To a 20 ml, Schlenk flask, a ligand compound (660 mg, 1.89 mmol/1.0 eq) obtained in Synthetic Example 2 and represented by Formula 2-2 and 10 ml (0.2 M) of MTBE were added and stirred. Then, n-BuLi (1.54 ml, 2.0 eq, 2.5 M in hexane) was added at −40° C., followed by reacting at room temperature overnight. After that, MeMgBr (1.29 ml, 2.0 eq, 3.0 M in diethyl ether) was slowly added dropwisely at −40° C., and $TiCl_4$ (1.88 ml, 1.0 eq, 1.0 M in toluene) was added thereto, followed by reacting at room temperature overnight. After that, a reaction mixture was passed through Celite using hexane for filtering. Solvents were dried to obtain 600 mg (75% yield) of a transition metal compound represented by the following Formula 1-2 as a brown solid.

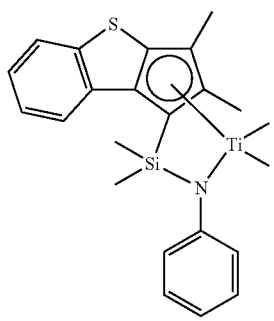

[Formula 1-2]

$^1$H NMR (in C$_6$D$_6$, 500 MHz): 7.93 (d, 1H), 7.45 (d, 1H), 7.22 (m, 3H), 7.10 (m, 2H), 6.98 (t, 1H), 6.92 (t, 1H), 2.10 (s, 3H), 1.95 (s, 3H), 0.77 (s, 3H), 0.60 (s, 3H), 0.50 (s, 3H), 0.28 (s, 3H).

Preparation Example 3: Synthesis of Transition Metal Compound Represented by Formula 1-3

To a 20 ml, Schlenk flask, a ligand compound (240 mg, 0.76 mmol/1.0 eq) obtained in Synthetic Example 3 and represented by Formula 2-3 and 4 ml (0.2 M) of MTBE were added and stirred. Then, n-BuLi (0.62 ml, 2.0 eq, 2.5 M in hexane) was added thereto at −40° C., followed by reacting at room temperature overnight. After that, MeMgBr (0.51 ml, 2.0 eq, 3.0 M in diethyl ether) was slowly added thereto dropwisely at −40° C., and TiCl$_4$ (0.76 ml, 1.0 eq, 1.0 M in toluene) was added, followed by reacting at room temperature overnight. After that, a reaction mixture was passed through Celite using hexane for filtering. Solvents were dried to obtain 194 mg (65% yield) of a transition metal compound represented by the following Formula 1-3 as a brown solid.

[Formula 1-3]

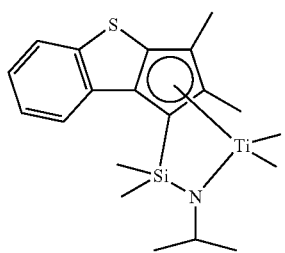

$^1$H NMR (in CDCl$_3$, 500 MHz): 7.96 (d, 1H), 7.46 (d, 1H), 7.09 (t, 1H), 6.56 (t, 1H), 4.87 (m, 1H), 2.13 (s, 3H), 1.90 (s, 3H), 1.25 (m, 3H), 1.11 (m, 3H), 0.61 (s, 3H), 0.57 (s, 3H), 0.46 (s, 3H), 0.04 (s, 3H).

Comparative Preparation Example: Preparation of tert-butyl(dimethyl(2,3,4,5-tetramethylcyclopenta-2,4-dien-1-yl)silyl)amino)dimethyltitanium To a 100 ml, Schlenk flask, a ligand compound, t-butyl (dimethyl(2,3,4,5-tetramethylcyclopenta-2,4-dien-1-yl)silyl)amine (2.36 g, 9.39 mmol/1.0 eq) obtained in Comparative Example and 50 ml (0.2 M) of MTBE were added and stirred. Then, n-BuLi (7.6 ml, 19.25 mmol/2.05 eq, 2.5 M in THF) was added at −40° C., followed by reacting at room temperature overnight. After that, MeMgBr (6.4 ml, 19.25 mmol/2.05 eq, 3.0 M in diethyl ether) was slowly added thereto dropwisely at −40° C., and TiCl$_4$ (9.4 ml, 9.38 mmol/1.0 eq, 1.0 M in toluene) was added, followed by reacting at room temperature overnight. After that, a reaction mixture was passed through Celite using hexane for filtering. Solvents were dried to obtain 2.52 g (82% yield) of a compound represented by the following formula as a yellow solid.

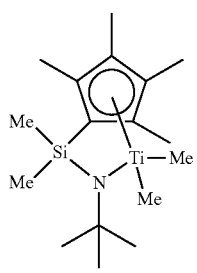

$^1$H NMR (in CDCl$_3$, 500 MHz): 2.17 (s, 6H), 1.92 (s, 6H), 1.57 (s, 9H), 0.48 (s, 6H), 0.17 (s, 6H).

Preparation Example of Polymer

A polymer was prepared using each compound prepared in Preparation Examples 1 to 3 and Comparative Preparation Example.

Example 1

A hexane solvent (1.0 L) and 1-octene (210 ml) were inserted to a 2 L autoclave reactor, followed by pre-heating the reactor to 150° C. At the same time, the pressure of the reactor was filled up with ethylene (35 bar) in advance. A dimethylanilinium tetrakis(pentafluorophenyl)borate co-catalyst (20 mol) and a transition metal compound (2.0 μmol) represented by Formula 1-1, prepared in Preparation Example 1 and treated with a triisobutyl aluminum compound were injected to the reactor while applying high pressure of argon (molar ratio of Al:Ti=10:1). Then, a copolymerization reaction was performed for 8 minutes. After that, the remaining ethylene gas was exhausted, and a polymer solution was added to an excessive amount of ethanol to induce precipitation. The precipitated polymer was washed with ethanol twice or three times, respectively, and dried in a vacuum oven at 90 for more than 12 hours to prepare a polymer.

Example 2

A polymer was prepared through the same method described in Example 1 except for using the transition metal compound represented by Formula 1-2 according to Preparation Example 2 instead of the transition metal compound according to Preparation Example 1.

Example 3

A polymer was prepared through the same method described in Example 1 except for using the transition metal compound represented by Formula 1-3 according to Preparation Example 3 instead of the transition metal compound according to Preparation Example 1.

Comparative Example

A polymer was prepared through the same method described in Example 1 except for using the transition metal compound according to Comparative Example instead of the transition metal compound according to Preparation Example 1.

Experimental Example

The physical properties of each polymer prepared in Examples 1 to 3, and Comparative Example were compared and analyzed. Evaluation results are shown in the following Tables 1 and 2.

1) Melt Index (MI)

Melt index of each polymer prepared in Examples 1 to 3, and Comparative Example was measured according to ASTM D-1238 (condition E, 190° C., 2.16 kg load).

2) Melting Temperature (Tm)

The melting temperature of each polymer prepared in Examples 1 to 3, and Comparative Example was obtained using a differential scanning calorimeter 6000 (DSC) manufactured by PerkinElmer Co. Particularly, about 0.5 mg to 10 mg of each polymer prepared in Examples 1 to 3, and Comparative Example was filled, and a nitrogen gas flow rate was controlled to 20 ml/min. In order to synchronize the thermal hysteresis of each polymer, the temperature of each polymer was increased from 0° C. to 150° C. at a rate of 20° C./min. Then, the peak of the heat curve of heat flow measured by DSC conducted while cooling the temperature from 150° C. to −100° C. at a rate of 10° C./min and then, elevating the temperature from −100° C. to 150° C. at a rate of 10° C./min. That is, the measurement was performed while regarding an absorption peak temperature during heating as the melting temperature.

3) Density

The density of each polymer prepared in Examples 1 to 3, and Comparative Example was obtained after manufacturing a sheet having a thickness of 3 mm and a radius of 2 cm using a press mold at 190° C., annealing thereof at room temperature for 24 hours, and measuring using a Mettler balance.

TABLE 1

| | Division | | |
|---|---|---|---|
| | Example 1 | Example 3 | Comparative Example |
| Yield (g) | 40.6 | 38.0 | 41.3 |

As shown in Table 1, it was achieved that the transition metal compounds (Examples 1 and 3) according to exemplary embodiments of the present invention exhibited similar yield when compared to the transition metal compound (Comparative Example) used as the conventional catalyst. From the results, it is confirmed that the transition metal compound according to an embodiment of the present invention has good activity as a catalyst.

TABLE 2

| | Division | | | |
|---|---|---|---|---|
| | Example 1 | Example 2 | Example 3 | Comparative Example |
| Melt index | 13.61 | 18.45 | 12.47 | 25.25 |
| Melting temperature | 89.97 | 40.1 | (51.05)/89.07 | 102.30 |
| Density | 0.890 | 0.863 | 0.872 | 0.904 |

As shown in Table 2, the polymers of Examples 1 to 3 prepared using the transition metal compound according to an embodiment of the present invention has a low density region and low melt index when compared to the polymer of Comparative Example prepared using the conventional CGC catalyst.

The invention claimed is:

1. A ligand compound represented by the following Formula 2:

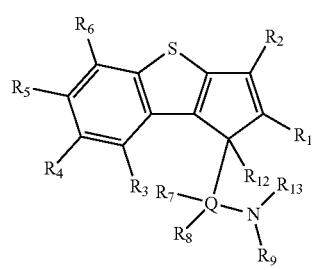

[Formula 2]

in Formula 2,
R$_1$ to R$_6$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, R$_7$ and R$_8$ are each independently hydrogen; alkyl having 1 to 20 carbon atoms; alkenyl having 2 to 20 carbon atoms; aryl having 6 to 20 carbon atoms; alkylaryl having 6 to 20 carbon atoms; arylalkyl having 7 to 20 carbon atoms; alkyl amido having 1 to 20 carbon atoms; aryl amido having 6 to 20 carbon atoms; or alkylidene having 1 to 20 carbon atoms, R$_9$ is hydrogen; alkyl having 1 to 20 carbon atoms; alkenyl having 2 to 20 carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms, two adjacent groups of R$_1$ to R$_9$ are optionally connected to each other to form a ring, R$_{12}$ and R$_{13}$ are each independently hydrogen, and Q is Si, C, N, P, or S.

2. The ligand compound of claim 1, wherein in the above Formula 2, R$_1$ to R$_6$ are each independently hydrogen; alkyl having 1 to 20 carbon atoms; aryl having 6 to 20 carbon atoms; alkylaryl having 7 to 20 carbon atoms; or arylalkyl having 7 to 20 carbon atoms, R$_7$ and R$_8$ are each independently hydrogen; alkyl having 1 to 20 carbon atoms; aryl having 6 to 20 carbon atoms; or alkylaryl having 6 to 20 carbon atoms, R$_9$ is hydrogen; alkyl having 1 to 20 carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms, two adjacent groups of $R_1$ to $R_9$ are optionally connected to each other to form an aliphatic ring having 5 to 20 carbon atoms or an aromatic ring having 6 to 20 carbon atoms, the aliphatic ring or the aromatic ring being substituted with halogen, alkyl having 1 to 20 carbon atoms, alkenyl having 2 to 20 carbon atoms, or aryl having 6 to 20 carbon atoms, $R_{12}$ and $R_{13}$ are each independently hydrogen, and Q is Si, C, N, or P.

3. The ligand compound of claim 2, wherein the compound represented by Formula 2 is represented by one of the following formulae:

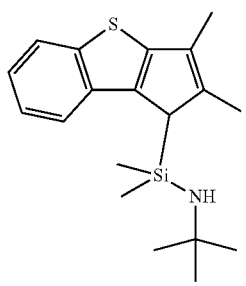

[Formula 2-1]

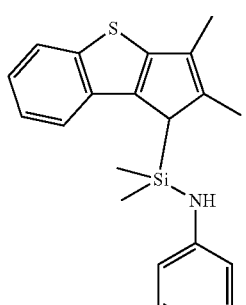

[Formula 2-2]

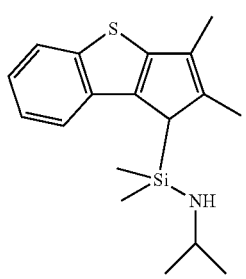

[Formula 2-3]

4. A method of preparing a ligand compound of Formula 2, the method comprising:
 a) preparing a compound represented by the following [Formula 3] by reacting a compound represented by the following [Formula 4] with a compound represented by the following [Formula 5]; and
 b) preparing a compound represented by the following [Formula 2] by reacting a compound represented by the following [Formula 3] with a compound represented by the following [Formula 6]:

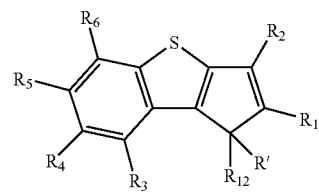

[Formula 4]

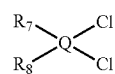

[Formula 5]

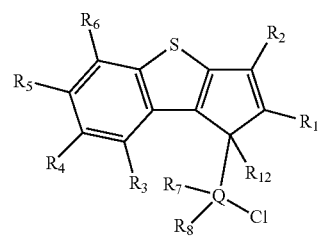

[Formula 3]

$R_9R_{13}NH$

[Formula 6]

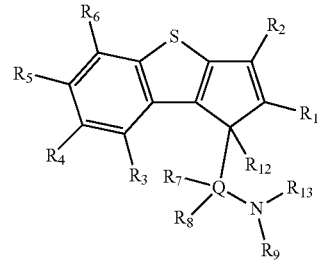

[Formula 2]

in the above formulae, $R_1$ to $R_6$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, $R_7$ and $R_8$ are each independently hydrogen; alkyl having 1 to 20 carbon atoms; alkenyl having 2 to 20 carbon atoms; aryl having 6 to 20 carbon atoms; alkylaryl having 6 to 20 carbon atoms; arylalkyl having 7 to 20 carbon atoms; alkyl amido having 1 to 20 carbon atoms; aryl amido having 6 to 20 carbon atoms; or alkylidene having 1 to 20 carbon atoms, $R_9$ is hydrogen; alkyl having 1 to 20 carbon atoms; alkenyl having 2 to 20 carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms, two adjacent groups of $R_1$ to $R_9$ are optionally connected to each other to form a ring, $R_{12}$ and $R_{13}$ are each independently hydrogen, and Q is Si, C, N, P, or S.

* * * * *